United States Patent [19]

Page et al.

[11] Patent Number: 5,369,699
[45] Date of Patent: Nov. 29, 1994

[54] ADAPTABLE PERSONNEL SUPERVISORY SYSTEM WITH AUTOMATIC FEE COLLECTION

[75] Inventors: David M. Page, Niwot; Elvin L. Riggs; Joseph P. Newell, both of Boulder; Vincent D. Stinton, Brighton, all of Colo.

[73] Assignee: BI Incorporated, Boulder, Colo.

[21] Appl. No.: 25,230

[22] Filed: Mar. 2, 1993

Related U.S. Application Data

[63] Continuation-in-part of Ser. No. 572,905, Aug. 23, 1990, Pat. No. 5,204,670.

[51] Int. Cl.5 .................. H04M 11/64; H04M 1/64; H04M 15/00; H04M 1/56
[52] U.S. Cl. ........................... 379/38; 379/67; 379/112; 379/117; 379/118; 379/142
[58] Field of Search ................ 379/38, 37, 49, 67, 379/112, 70, 71, 117, 118, 142

[56] References Cited

U.S. PATENT DOCUMENTS

| | | |
|---|---|---|
| 3,253,588 | 5/1966 | Vuilleumier et al. |
| 3,478,344 | 11/1969 | Schwitzgebel et al. ............ 340/312 |
| 3,618,067 | 11/1971 | DeVale et al. ............ 340/282 |
| 3,639,907 | 1/1972 | Greatbatch . |
| 3,764,270 | 4/1973 | Collier ............ 23/255 |
| 3,882,277 | 5/1975 | DePedro et al. ............ 179/2 DP |
| 3,882,278 | 5/1975 | Coll ............ 179/5 R |
| 3,898,984 | 8/1975 | Mandel et al. ............ 128/2.1 A |
| 3,947,832 | 3/1978 | Rosgen et al. ............ 390/224 |
| 4,112,421 | 9/1978 | Freeny, Jr. ............ 343/112 D |
| 4,136,338 | 1/1979 | Antenore ............ 340/551 |
| 4,259,665 | 3/1981 | Manning ............ 340/575 |
| 4,260,982 | 4/1981 | DeBenedictis ............ 340/539 |
| 4,342,986 | 8/1982 | Buskirk et al. ............ 340/539 |
| 4,347,501 | 8/1982 | Akerberg ............ 340/539 |
| 4,371,752 | 2/1983 | Matthews et al. ............ 179/7.1 TP |

(List continued on next page.)

FOREIGN PATENT DOCUMENTS 965179 3/1975 Canada ............ 349/31

OTHER PUBLICATIONS

Schwitzgebel, R. K., "Issues in the use of an Electric Rehabilitation System with Chronic Recidivists", *Law and Society Review*, 3:597–611 (1969).

(List continued on next page.)

*Primary Examiner*—Stephen Chin
*Assistant Examiner*—Paul Loomis
*Attorney, Agent, or Firm*—Fitch, Even, Tabin & Flannery

[57] ABSTRACT

A supervisory system and method automatically tracks and reports the status, e.g., current address, employer, telephone number, etc., of a group of enrollees, and automatically collects a fee for such service. Each enrollee "reports in" to a host CPU of the system in accordance with a specific contact schedule, e.g., once a month, through a fee-based telephone network that automatically charges a prescribed toll fee to the originating telephone number whenever telephone contact remains established for more than a preamble time period. The host CPU, using individual calling line identification (ICLID) information included in the incoming telephone call, identifies the telephone number of the incoming call and determines if it belongs to an enrollee of the system. If not, the incoming call is disconnected before the preamble time period expires, thereby preventing the incoming caller from being charged the toll fee. Further, if a given enrollee attempts to report in more than once during the same reporting period, the incoming call is disconnected before the preamble time period expires, thereby preventing the incoming caller from being charged the toll fee more than once for a given reporting period. When valid telephone contact is established, the identify of the caller is verified to make sure it is an enrollee, and the verified enrollee then updates the status information, if needed. Reports are generated to selectively indicate which enrollees have or have not reported during the prescribed reporting period, and any change in their status.

33 Claims, 5 Drawing Sheets

U.S. PATENT DOCUMENTS

| | | | |
|---|---|---|---|
| 4,428,378 | 1/1984 | Anderson et al. | 128/419 |
| 4,475,481 | 10/1984 | Carroll | 119/51 R |
| 4,494,119 | 1/1985 | Wimbush | 343/457 |
| 4,494,553 | 1/1985 | Sciarra | 126/721 |
| 4,559,526 | 12/1985 | Tani et al. | 340/539 |
| 4,593,273 | 6/1986 | Narcisse | 340/539 |
| 4,598,275 | 7/1986 | Ross et al. | 340/573 |
| 4,622,544 | 11/1986 | Bially et al. | 340/636 |
| 4,631,708 | 12/1986 | Wood et al. | 367/2 |
| 4,656,463 | 4/1987 | Anders et al. | 340/572 |
| 4,658,357 | 4/1987 | Carroll et al. | 364/406 |
| 4,665,387 | 5/1987 | Cooper et al. | 340/572 |
| 4,675,656 | 6/1987 | Narcisse | 340/539 |
| 4,709,704 | 8/1987 | Lukasiewicz | 128/644 |
| 4,747,120 | 5/1988 | Foley | 379/38 |
| 4,814,751 | 3/1989 | Hawkins et al. | 340/573 |
| 4,819,860 | 4/1989 | Hargrove et al. | 228/668 |
| 4,827,943 | 5/1989 | Bornn et al. | 128/668 |
| 4,837,568 | 6/1989 | Snaper | 340/825 |
| 4,843,377 | 6/1989 | Fuller et al. | 340/573 |
| 5,023,901 | 6/1991 | Sloan et al. | 379/38 |
| 5,054,055 | 10/1991 | Hanle et al. | 379/142 |

OTHER PUBLICATIONS

Ingraham, et al., "Controlling Human Behavior with Electronics", *The Futurist,* pp. 60–62 (1970).

Schwitzgebel, et al., "Methods and Designs", *Behav. Res. Meth. & Instru.,* 2:99–105 (1970).

Meyer, "Crime Deterrent Transponder System", *IEEE Transactions on Aerospace and Electronic Systems,* AES-7:1, 2–22 (Jan. 1971).

Schmidt, et al., "Electronic Monitors", in Intermediate Punishments: Intensive Supervision, Home Confinement and Electronic Surveillance; *Issues in Crime and Justice,* 2:137–152 (Belinda R. McCarthy, Editor) (Criminal Justice Press, Monsey, N.Y. 1987).

Vaughn, "Planning for Change: The Use of Electronic Monitoring as a Correctional Alternative", in Intermediate Punishments: Intensive Supervision, Home Confinement and Electronic Surveillance: *Issues in Crime and Justice,* 2:153–168 (Belinda R. McCarthy, Editor) (Criminal Justice Press, Monsey N.Y. 1987).

ADAPTABLE PERSONNEL SUPERVISORY SYSTEM WITH AUTOMATIC FEE COLLECTION

This application is a continuation-in-part of U.S. application Ser. No. 07/572,905, filed Aug. 8, 1990, U.S. Pat. No. 5,204,670.

BACKGROUND OF THE INVENTION

The present invention relates to an adaptable personnel supervisory system having automatic fee collection capabilities. Such a supervisory system may be used for a wide variety of applications, including monitoring and supervising those who are on probation, parole, or on pretrial status. However, the system can be readily adapted for use in fields other than probation, parole, or pretrial, such as child support, medical, home health care, security and similar systems where individuals need to be monitored and supervised, and where a fee is to be charged and collected for such monitoring and supervision, or where a fee is to be charged and collected for related fines, restitution, child support, or services.

Probation was established in the United States as an "alternative sentence" around 1900. Originally intended only for first time and non-violent offenders, probation has long since outstripped institutional imprisonment in popularity as a judicial disposition, and is now clearly the sentence of choice. Despite media attention to institutional overcrowding, the number of probation cases is rising much more rapidly than the number of those sentenced to prisons, jails, or on parole.

When an offender is sentenced to "probation", he is effectively placed under the watch care of a "probation officer", (also referred to herein as a "parole officer") and is required to regularly report to the probation officer for a specified probation time period concerning his whereabouts, current employment, address, telephone number, and the like. A given "parole officer" may also be called upon to supervise or watch over those on "parole" in much the same manner, regularly obtaining the same basic information concerning the parolee's activities and whereabouts. Such reported information is referred to herein as the "status" of the probationer or parolee. Further, the term "officer" is used herein to describe the individual responsible for supervising those on probation, parole or pretrial, or others being supervised, even though such individual may have a title different than probation officer.

The caseload of the average probation officer continues to grow rapidly. For example, in Los Angeles County, two-member teams of probation officers must supervise as many as 2,000 cases each. In New York City, each probation officer has a caseload of about 225. Other cities and areas show similar high caseload numbers. In 1990, there were 2.7 million adults on probation (up 5.9% during the year) and 531,000 on parole (up 16.3% during the year).

Unfortunately, when the caseload of a probation officer goes up, the effectiveness of using probation as a tool for providing community protection, or as a means of punishment or control, diminishes. What is needed, therefore, is a more effective system for allowing a probation officer, or team of probation officers, to more competently handle an increasing caseload.

Because there is a significant expense associated with monitoring those who have been sentenced to probation or parole, most jurisdictions in the United States have now authorized some form of correctional fees. Specifically, statutes have been passed in over 28 states that authorize the collection of a fee for those on probation, and in over 15 states that authorize the collection of a fee for those on parole. The recent flurry of legislative activity, coupled with strapped state budgets, suggests that collecting fees from those on probation or parole will continue to be a popular mechanism for supplementing the corrections budget. Significantly, while not everyone favors collecting such fees, much of the opposition comes from those who believe too much time is spent on collection of fees rather than on supervising offenders. Hence, there is a significant need to reduce the time that probation officers spend in collecting statutory fees from offenders, thereby freeing up such officers to fulfill the supervisory function for which they were hired.

The monthly supervision fees charged by probation and parole agencies vary from $10 to $265, with the average monthly fee being between $20 and $26. The effective collection rate achieved by the agencies responsible for such collection is difficult to determine, but is probably less than about 50%. In many situations, probation officers have been asked to perform the duties of a collection agent in order to attempt to collect fees that are owed. Disadvantageously, this has the effect of further overburdening overworked officers, and results in diluted supervision efforts. Additionally, because of budgetary concerns, i.e., in situations where the corrections agency must collect the fees in order to stay in business, trained corrections professionals are sometimes asked to be collection agents—a job for which they are not trained nor have interest. Hence, when the agencies are forced to make this request, they end up losing the time of trained corrections professionals in exchange for untrained and possibly unmotivated collection agents. There is thus a critical need in the corrections industry for a simple, yet effective, system or method for collecting the supervision fees that are owed by the offenders without requiring that probation officers or trained corrections professionals function as collection agents ("bill collectors").

SUMMARY OF THE INVENTION

The present invention addresses the above and other needs by providing a supervisory system that integrates the reporting function, wherein those being supervised must regularly report their status to an officer, with the fee collection function, which requires that a prescribed fee be collected from those being supervised. Advantageously, the system allows the officer to efficiently handle large caseloads without being concerned with the collection of fees. This it does by automatically charging the assessed fee to the supervised person each time that the supervised person reports to the officer or at one or multiple times during a defined reporting period, which fee is thereafter automatically included in the supervised person's telephone bill.

In accordance with one aspect of the invention, a supervisory system and method is provided that automatically tracks and reports the status, e.g., current address, employer, telephone number, etc., of a group of enrollees, and automatically collects a fee for such service. Each enrollee is required to "report in" to the system by telephone in accordance with a specific contact schedule, e.g., once a month. The system includes a host CPU that is coupled to a fee-based telephone network, e.g., a "900" telephone number. A prescribed toll fee is automatically charged to the originating telephone number of any incoming telephone call received at the CPU through the fee-based telephone number whenever the telephone contact remains established for more than a preamble time period (e.g., 19 seconds). The host CPU also includes appropriate circuitry, such as automatic number identification (ANI) circuitry, or caller ID circuitry, that identifies the telephone number of any incoming telephone call. Such circuitry, e.g., uses the individual calling line identification (ILCID) information, or equivalent information, now included on most incoming telephone calls. The valid telephone numbers of all those enrolled in the system are stored in a data base within a memory of the host CPU. If an incoming telephone call has not originated from a valid telephone number, it is disconnected before the preamble time period expires, thereby preventing the incoming caller from being charged the prescribed toll fee. Further, the host CPU keeps track of which enrollees have reported in during the current reporting period, as set by the prescribed contact schedule, and which have not. Advantageously, if a given enrollee attempts to report in more than once during the same reporting period, the incoming telephone call is also disconnected prior to the expiration of the preamble time period, thereby preventing the incoming caller from being charged the toll fee more than once for a given reporting period.

In accordance with another aspect of the invention, once telephone contact has been established with the host CPU from a valid telephone number pursuant to the prescribed contact schedule, the host CPU verifies the identify of the caller through the use of a personal identification number (PIN), a voice print, or other suitable identification means. With the identity of the caller having been verified to be that of a particular enrollee, the enrollee is then asked, using speech generation circuitry also included in the host CPU, to update any changes in his or her status since the last time that the enrollee reported. Such status information is updated by having the enrollee respond to a series of YES/NO questions that the enrollee answers by activating an appropriate key or number on his or her telephone, or by speaking YES or NO (if calling from a rotary phone). As needed, any particular YES or NO answer may be supplemented with additional spoken information. The status information thus provided by the enrollee is used to update the status information already stored in the host CPU for that particular enrollee. Reports are generated by the host CPU, as requested by the officer or other supervisory personnel, to selectively indicate which enrollees have not reported during the prescribed reporting period, which have reported, and of those who have reported, any change in their status.

The present invention, in accordance with one characterization thereof, may be described as an adaptable personnel supervisory system (PSS). Such PSS includes: (1) a fee-based communication network that automatically charges a toll fee to a user thereof once telecommunicative contact has been established through the fee-based communication network with a host unit for a specified preamble time period; (2) a central processing unit (CPU) coupled to the fee-based communication network; (3) a memory coupled to the CPU having enrollment data stored therein that identifies enrollees who are under an obligation to contact the PSS in accordance with a prescribed contact schedule; and (4) control means for controlling the operation of the CPU to provide a desired supervisory function. The control means includes answering means for automatically answering an incoming call over the fee-based telephone network; and call verification means for verifying, before the expiration of the preamble time period, whether the incoming call is a valid call, and if not for terminating the incoming call before the toll fee is charged. A valid call comprises an incoming call that originates from one of the enrollees in accordance with the prescribed contact schedule. Thus, the toll fee is not charged unless the incoming call is valid. The control means further includes prompting means responsive to the verifying means for prompting a given enrollee who has made a valid call to the PSS to provide selected information, e.g., status information. Also included within the control means are recording or storage means for recording or storing any selected information provided by the given enrollee in response to the prompting means; and report means for selectively generating host reports that selectively identify which enrollees have not made contact with the host unit, which enrollees have made contact with the host unit, and the selected information provided by the enrollees who have made contact with the host unit. Thus, each enrollee is automatically charged the toll fee whenever he or she contacts the PSS by means of a valid call placed through the fee-based communication network in compliance with the prescribed contact schedule.

Another characterization of the invention is that of an adaptable personnel monitoring and identification system used for monitoring a population of individuals. Such monitoring and identification system includes means for establishing telecommunicative contact between a given individual within the population of individuals and a central processing unit (CPU). The given individual is under an obligation to make regular status reports to the CPU through the established telecommunicative contact. The CPU has status information stored therein for each monitored individual. The CPU also has an administrative case load management program stored therein. Such administrative case load management program includes means for verifying the identity of the given individual once telecommunicative contact is established with the CPU, and means for automatically requesting whether the status information stored in the CPU for the given individual has changed since the given individual last contacted the CPU. Further, such monitoring and identification system includes means for automatically charging the given individual with a prescribed fee once the identify of the given individual has been verified.

In accordance with still another characterization, the invention may be viewed as a method of automatically charging a fee to an enrollee of a supervisory system whenever the enrollee makes telephone contact with a host CPU of the supervisory system in accordance with a prescribed telephone contact schedule. The method comprises the steps of: (a) assigning a specific fee-based telephone number to the host CPU, the fee-based telephone number being controlled through a telephone network so as to automatically charge a prescribed fee to a caller who calls the specific fee-based telephone number and remains in contact with the host CPU via the specific fee-based telephone number for more than a prescribed preamble time period; (b) storing enrollment data in a memory of the host CPU that identifies each enrollee and his or her telephone number from which the specific fee-based telephone number is to be called; (c) monitoring the incoming calls received at the host CPU (each of which includes individual calling line identification information) during the preamble time period to determine if they have originated from an enrollee's telephone number; (d) automatically disconnecting, prior to the timing out of the preamble time period, any incoming call received through the specific fee-based telephone number that did not originate from one of the enrollee's telephone numbers as determined in step (c), thereby not charging the prescribed fee to an incoming call from any number other than one of the enrollee's telephone numbers; (e) generating a speech message at the host CPU in response to any incoming call received through the specific fee-based telephone number that did originate from one of the enrollee's telephone numbers, the speech message instructing the given enrollee how to inform the host CPU of his or her current status, including whether such status has changed since the given enrollee last contacted the host CPU. Advantageously, the speech message and any corresponding response from the given enrollee lasts longer than the preamble time period, thereby automatically charging the prescribed fee to an enrollee who places an incoming call to the host CPU through the specific fee-based telephone number.

It is thus a general feature of the invention to provide a supervisory and/or collection system and method that allows a probation officer, or other supervisory personnel, to effectively handle and supervise a large caseload.

It is another general feature of the invention to provide such a supervisory and/or collection system that automatically charges a prescribed fee for the supervision services provided by the system.

It is a further feature of the invention to provide a fee-based supervisory and/or collection system wherein supervisory personnel are free to spend their time in supervising those enrolled in the system, and do not have to spend any time in collecting supervision fees.

It is an additional feature of the invention to provide a supervisory and/or collection system that is especially well suited to the corrections industry, allowing probation officers and corrections professionals to monitor a large caseload of probationers and/or parolees, while at the same time automatically charging an appropriate fee to the probationers and/or parolees who are monitored.

It is another feature of the system to provide a mechanism by which fees not necessarily related to supervision, such as fines, restitution, child support, and the like, can be readily collected.

It is yet another feature of the invention to provide a fee-based supervisory and/or collection system wherein the supervisors do not have to be bill collectors.

It is yet another feature of the invention to provide a supervisory and/or system and method that is inexpensive to acquire and easy to install, operate and maintain.

It is still a further feature of the invention to provide a fee-based supervisory and/or collection system that regularly or on command generates reports showing the status and compliance with mandated reporting and/or payment schedules of all or selected enrollees.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1:
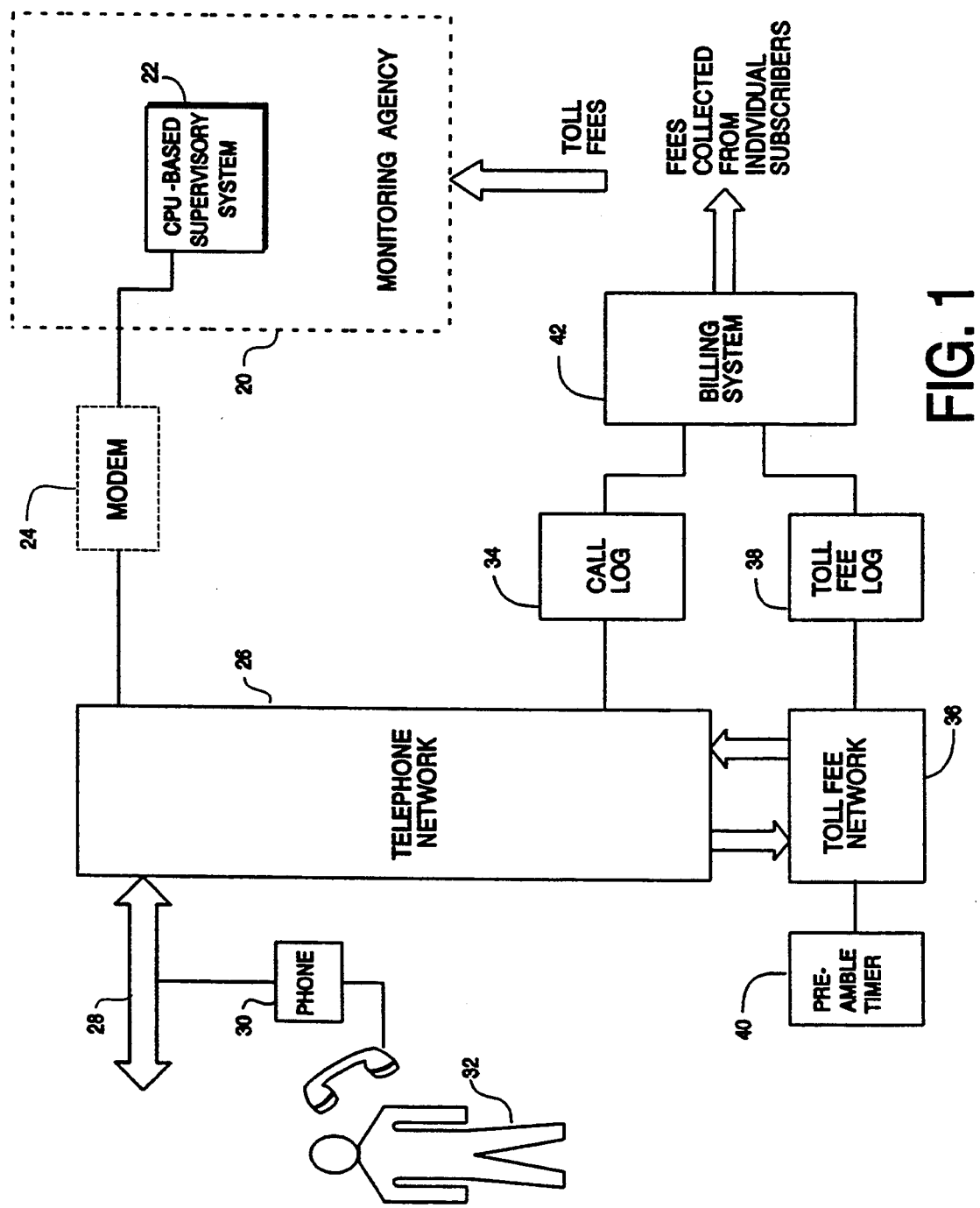
FIG. 1 shows a block diagram of a fee-based supervision system made in accordance with the present invention.

The following description is of the best mode presently contemplated for carrying out the invention. This description is not to be taken in a limiting sense, but is made merely for the purpose of describing the general principles of the invention. The scope of the invention should be determined with reference to the claims.

An adaptable personnel monitoring and identification system is described in copending application Ser. No. 07/572,905, filed Aug. 23, 1990, U.S. Pat. No. 5,204,670, which patent is incorporated herein by reference (hereafter the "parent" patent). The system described in such patent provides a useful supplement to the invention described herein.

As described in the parent patent, an adaptable personnel monitoring and identification system includes a large selection of software submodules, or equivalent control programs, that allow a particular agency to adapt the monitoring and identification system to best suit its particular needs and requirements. One such submodule is referred to as the administration case load management submodule. Such submodule allows the administrative agency to keep track of a large population of personnel who are on the "back end" of the agency's responsibility. Such personnel are generally considered low risk, and are under obligation to contact the agency periodically, e.g. every week, every month, or every year, to advise the agency of their current status. Such personnel need not carry or wear a tag with a built-in transmitter, as described in the parent patent. All they need do is send a postcard, pick up a telephone or make a personal visit to their assigned agency officer. When contact is established with the agency, which will usually be by telephone (but it could also be via mail or a personal visit) the agency officer asks them certain basic questions, such as if their address is the same, if their employer is the same, and if they have been arrested for any reason during the past period since last contacting the agency. If there have been changes, the officer makes note of the same and updates their file.

At present, the function of administration case load management is handled manually, assisted as required by a computer, by each agency. This represents a significant burden for some agencies as the number of personnel on "back end" supervision can be quite large. For example, in Los Angeles County, Cal., it is estimated that over fifty-five percent of those on probation (which is a large number, i.e., over 50,000) are on "back end" supervision. On average, this population of supervised personnel must contact the agency once a month. Thus, there are some 50,000 phone calls (or other contact) that agency personnel must make each month in monitoring the status of this "back end" population.

The present invention advantageously allows back-end supervision to be performed automatically by a host computer, maintained and operated by the monitoring agency (or a service company hired by the monitoring agency), using appropriate administrative case load management software, and further allows the agency to automatically collect a fee when such supervision is performed, if such fee has been authorized. When this option is included in the system, a computer file is maintained for each of the monitored persons. This file contains the basic status information. The monitored person must make contact with the host computer at the regularly scheduled interval, e.g., once a week, once a month, or once a year. Such contact will typically be accomplished over a conventional telephone line, but it is understood that any telecommunicative contact could be made. For example, where telephone contact is established between the monitored person and the agency's host computer, the person may be given an 800 telephone number for making contact with the computer, so that the person incurs no telephone charges for making the call. As explained below, if a fee has been authorized, then a fee-per-call telephone number is used, such as a 900 telephone number, and the person is automatically charged the fee each time that he or she reports to the agency.

When contact is made, the host computer screens the person making contact to make sure of the person's identify, and in some instances (e.g., where the person is supposed to remain in a certain geographic area) that the person is within an assigned area where the contact is made. In particular, using conventional automatic number identification (ANI) features, now widely available through most telephone networks and local telephone companies, the host computer is able to readily ascertain if the caller is calling from a particular phone number, i.e., that the caller is where he or she is supposed to be.

In general, the system may provide three possible levels of screening when contact is made with the host computer. In a first level of screening, for example, the computer, through voice synthesis or equivalent voice generation circuits, will ask the person to identify himself or herself. Such identification will normally be accomplished by the person keying into the telephone a personal identification number (PIN) and/or password. The computer may be programmed to recognize such PIN regardless of whether it is keyed into a touchtone telephone or spoken to a rotary dial telephone. Once the computer has identified the caller and verified that the caller is a valid caller, e.g., that a valid PIN and/or password has been received, it asks whether there have been any changes to the status of the caller since last making contact. The caller may respond by keying in a "1" for YES (or saying "YES") or a "2" for NO (or saying "NO"). To help the caller remember what information the computer has on file, the computer may, prior to asking this question, repeat what information it has. That is, as soon as a valid PIN is received, the computer may respond with the person's name, address, and employer as stored in the computer memory files. If the person responds with a YES, indicating that there has been a change in his or her status since the last contact, then the person is requested to speak into the telephone what the changes are, e.g., a new address or a new employer. This new information is recorded for later review by agency personnel, who key it into the host CPU memory files. Some embodiments, adapted for use with touch-tone phone service, allow the person to key in the updated status information directly to the computer using the touch-tone key pad of the telephone. Still other embodiments provide for automatic transcription of the responses provided.

In a second level of screening, which may be an option for use with the first level of screening, the caller is further identified through his or her voice. In such screening, the computer has on file a previously entered sample of the individual's voice. The computer thus compares the voice spoken when the telecommunicative contact is established with the voice stored for the person having the PIN entered by the person. If there is a match, the person is allowed to continue with the updating of the status information. If there is not a match, that fact is noted, and a report is generated for the agency officer alerting him or her to the fact that someone other than the proper individual having a prescribed PIN attempted to contact the CPU for purposes of their regular check-in.

A block diagram of a personnel supervisory system (PSS) made in accordance with the present invention is shown in FIG. 1. As seen in FIG. 1, the system includes a monitoring agency 20 having at least one host computer 22 connected through a suitable connection, which may include a modem 24, to a conventional telephone network 26. The host computer 22 is configured to function as a CPU-based supervisory system. Such system typically includes several individual computers linked together through a local area network (LAN). The telephone network 26 allows telephone calls to be placed from any telephone in telecommunicative contact with the network 26 over telephone communication lines 28 (which may be actual telephone wires, a cellular based communication line, a satellite link, or any other suitable communication link) to any other telephone connected to the network over such lines 28, or through other telephone networks, in conventional manner.

The telephone network 26 includes means for maintaining a call log 34 that keeps track of the number and types of calls that are made from a given telephone number. The information contained in such log is then input into a billing system 42, so that the telephone company that manages the telephone network can periodically send bills to those who use the telephone service (referred to in FIG. 1 as the "subscribers" of the telephone service). Telephone calls are typically billed as a function of whether the call is a local call, or whether it is a long distance call. Long distance calls are billed at differing rates depending upon the time of day the call is made and/or the distance between the calling parties.

The telephone network 26 also includes, or is coupled to, a toll fee or premium charge network 36. A toll fee (or premium charge) network is really no different than the regular telephone network except that a prescribed toll fee or charge is automatically charged to the calling party each time that a call is made through the toll fee (premium charge) network. Typically, in the United States and Canada, most toll fee or premium charge calls are accessed by dialing a "900" telephone number, e.g., a telephone number where the three digit area code is replaced by "900". When a "900" number is dialed by a user, the telephone network makes telephone contact with the dialed "900" number in conventional manner. Immediately following the first ring signal associated with an incoming call into the CPU-based supervisory system., a preamble timer 40 begins a prescribed time interval, e.g., 18 seconds. Should telephone contact be established and still be intact at the conclusion of the prescribed time interval, i.e., so long as either party doesn't "hang up" before the timing out of the prescribed time interval, then a toll fee log 38 records that the toll fee call was completed, and the prescribed toll fee is incorporated by the billing system 42 with the fees included in the calling party's normal telephone bill. The subscriber of the telephone network thus pays the toll fee or premium charge with his or her normal telephone bill. The telephone company, or other agency that collects the telephone bill payments from the subscribers, then forwards a defined portion of the toll fee to the particular agency or service company who provides a service to the calling party through the toll-fee number. Toll-fee numbers, e.g., 900 numbers, are typically used to provide specific information or services for a given caller, e.g., sports scores, stock prices, travel information, and the like. For purposes of the present invention, it is to be understood that the invention is not limited to the use of "900" toll fee network, but may be used with any type of toll fee or premium charge network that automatically charges a prescribed toll fee each time the toll fee network is accessed. Alternatively, it is noted that the versatility of the present invention allows the service provider to keep track of a premium charge log (i.e., a list that identifies the subscribers who have called in), and to provide the telephone company with billing information which can be subsequently included on the subscriber's bill.

In accordance with the present invention, a toll-fee number is assigned to the particular monitoring agency (or group of monitoring agencies) 20 responsible for supervising a population of individuals, e.g., those on parole and/or probation. Each supervised individual 32 belonging to the group of supervised individuals, is under an obligation to make telephone contact with the monitoring agency 20 from an assigned telephone 30 using the toll-fee number of the agency in accordance with a prescribed contact schedule, e.g., once a month. Because the individual 32 being supervised is typically required to remain within a prescribed area, the assigned telephone 30 will be one within such prescribed area. For convenience, the assigned telephone 30 may be the one at the individual's residence or place of employment.

The monitoring agency 20 manages the host CPU supervision system 22 so as to keep track of all the individuals 32 being supervised. At a minimum, the CPU supervision system 22 includes data stored therein that identifies, for each individual being supervised, the assigned telephone number from which the individual is supposed to call when reporting to the agency, and the address and place of employment of the individual. As explained more fully below, when the individual makes a call through the toll-fee network 36 to the monitoring agency 20 in accordance with the prescribed contact schedule, the CPU supervision system 22 determines if such call is a "valid" call. A valid call is one which has originated from one of the assigned telephone numbers stored in the memory of the CPU supervision system 22, and which has been made in accordance with the prescribed schedule. If the incoming call at the CPU is not a valid call, then the CPU disconnects the call, i.e., "hangs up" before the expiration of the preamble time period, thereby preventing the caller from being charged the toll fee for an invalid call. If the call is a valid call, then the CPU supervision system 22 allows telephone contact to remain intact, so that the toll fee is charged to the caller, and asks the caller if there has been any change in his or status since the last time the caller reported to the agency. If so, then the caller is afforded the opportunity to update his or her records, as stored in the CPU-based supervisory system 22, in order to reflect the change in status. If not, then the caller is reminded of when next a report is due. The manner in which such process is carried out is explained in more detail below in connection with the description of FIGS. 3–5.

Significantly, as illustrated in FIG. 1, the monitoring agency 20 collects its portion of the toll fees from the telephone company, or other agency that receives payment from the subscribers of the telephone network. Thus, agency personnel need not be skilled in the art of "bill collecting", but can rather devout their full-time efforts to the supervision function for which they are trained.

Figure 2:
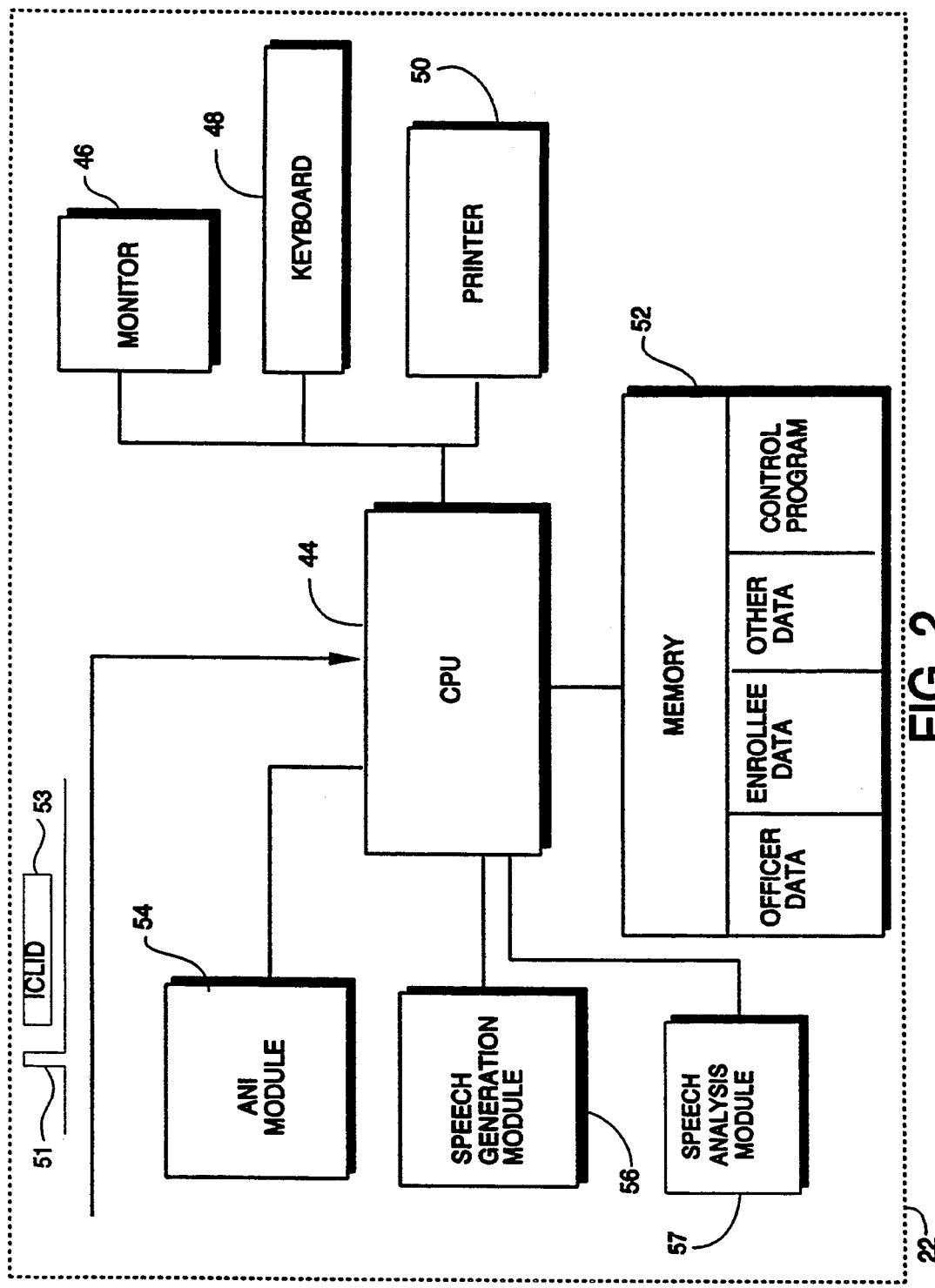
FIG. 2 shows a block diagram of the host computer of the fee-based supervision system of FIG. 1.

Turning next to FIG. 2, a block diagram of the CPU-based supervisory system 22 is illustrated. As seen in FIG. 2, such system 22 includes a central processing unit (CPU) 44 coupled to a memory 52. The memory 52 includes a control program that controls the operation of the supervision system 22 as explained more fully below. The memory 52 also has officer data, enrollee data, and other data stored therein that allows the system to be configured appropriately. The enrollee data includes personal data for each person enrolled in the system, i.e., each individual that is to be supervised by the system. The officer data includes personnel data that identifies a particular officer responsible for supervising a given enrollee or group of enrollees. Such data facilitates the making and delivery of reports for such officer relative to how many of the enrollees have reported on schedule, how many have not reported, etc., and further allows such officer to customize his or her reports as needed. Moreover, such data allows a given officer to leave a personalized message for a given enrollee that the system 22 will deliver to the enrollee the next time that the enrollee reports to the system. Other data may also be stored in the memory 52, e.g., the digitized responses of the enrollees to specific questions, a call-in log, and the like.

Also coupled to the CPU 44 is an automatic number identification (ANI) module 54, a speech generation module 56, and a speech analysis module 57. The ANI module 54 includes conventional circuitry that allows the CPU to quickly identify the telephone number of an incoming telephone call. The module 54 may include ANI circuitry that uses a control channel (commonly referred to as a "D channel") in parallel with a plurality of communication channels or lines, e.g., 23 lines, that identifies the source of an incoming call on a particular incoming line. Alternatively, the module 54 may include "caller ID" technology wherein incoming call line identification data is provided by the telephone network 26 (FIG. 1) immediately after a first ring of an incoming call. Caller ID circuits are known in the art, see, e.g., U.S. Pat. No. 5,054,055, incorporated herein by reference. Whatever type of circuitry is used within the module 54, it performs the function of identifying the source of the incoming call, i.e., the telephone number from which the call originated. Such identification is referred to herein as incoming call line identification (ICLID) data, and such ICLID data is schematically depicted in FIG. 2 as a block 53 that follows the first ring depicted as a pulse 51. Advantageously, the ICLID data 53 (whether it follows the first ring 51 as shown in FIG. 2, or whether it is available on a separate control channel concurrent with the first ring) can be retrieved and analyzed by the ANI module 54 of the CPU 44 before the timing out of the preamble time period associated with the incoming toll call.

The speech generation module 56 includes conventional circuitry that generates appropriate voice signals that can be heard by the enrollee through his or her telephone, just as though the enrollee were talking to a live person. Such circuitry allows the supervisory system 22 to ask the enrollee certain questions concerning his or her status, and further allows the system to give the enrollee needed information, such as why his or her call is not a valid call, or when the next scheduled report is due.

The speech analysis module 57, when used, compares the voice print of selected words or phrases spoken by the caller with pre-recorded voice prints of the caller stored in the memory 52. Such voice prints are thus used to help identify that the caller is the enrollee and not an imposter.

Further coupled to the CPU 44 is a monitor 46, a keyboard 48 and a printer 50, and any other peripheral equipment that the agency 20 may see fit to utilize. It is through such devices that officer and enrollee data is initially entered into the system, and through which appropriate reports are generated. As indicated, the CPU 44 may actually comprise several CPU's that are coupled together through an appropriate local area network (LAN).

The operation of the supervision system will next be explained in conjunction with the flow charts shown in FIGS. 3–5. Such flow charts show each main step carried out by the system 22 as it automatically performs its supervision function. For convenience of explanation, each main step is enclosed within a "box" or "block" having a reference numeral. Rectangular-shaped blocks represent a particular step or function that is performed, and hexagonal-shaped (or sometimes diamond-shaped) blocks represent a decision or determination that is made.

Figure 3:
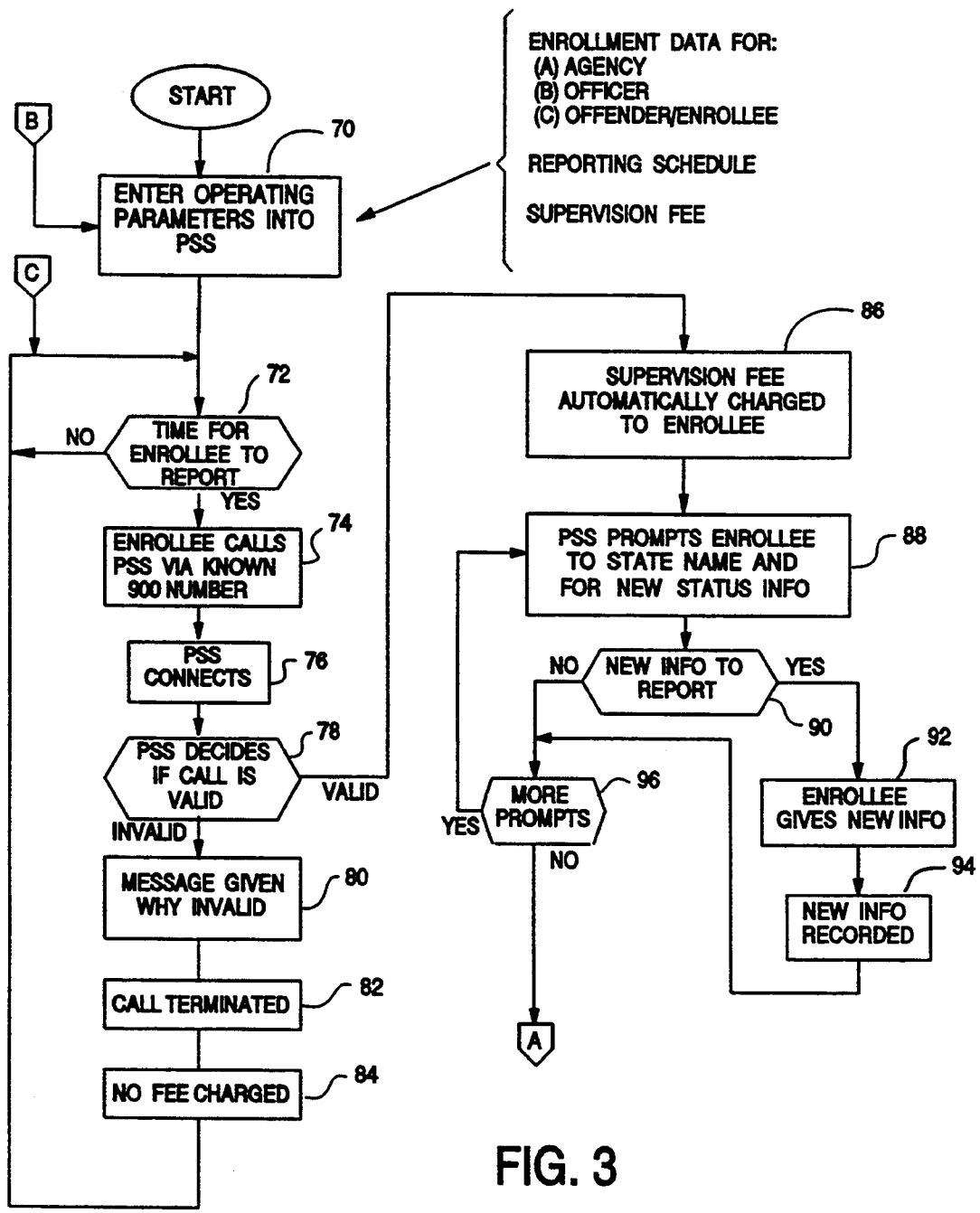
FIG. 3 is a flow chart that illustrates the operation of the fee-based supervision system of FIG. 1.

Referring to FIG. 3, a first step of the operation (block 70) requires that operating parameters be entered into the personnel supervisory system (PSS). Such operating parameters include enrollment data. Agencies, officers and offenders are enrolled in the PSS. Agencies enter into appropriate agreements with those administering the telephone (or other communication) system, including the toll-fee network. Typically, a service company, such as BI Incorporated, of Boulder Colorado, who has already established a contractual relationship with the telephone company and those offering the 900 toll (fee-per-call) service, establishes a contractual relationship with a plurality of monitoring agencies to perform and report their monitoring functions. The service agency thus serves as a central location where all calls are directed, maintains the CPU-based supervisory system 22 (FIG. 1), including the records of the enrollees. The agency then simply links to such service company through a conventional networking system. Thus, the "monitoring agency" 20 shown in the block diagram of FIG. 1 may actually comprise a service company that provides the supervision service to a large number of agencies that contract for such service.

Officers of the agency also enroll in the system. Once enrolled, an officer can enroll offenders (or other enrollees who are to be supervised), send voice mail to enrollees, and receive exception reports (any changes in the status of an enrollee) and missed call reports. The officer enrollment process typically includes completion of an officer enrollment form that identifies the officer's name and the agency to which the officer belongs. In addition, during enrollment an officer personal identification number (PIN) is assigned to the officer, and the officer selects a password known only to him or her. Further, a code is assigned to identify the agency. Finally, the address and phone number of the agency, as well as the phone number of the officer, are also recorded. All of this "officer enrollment" data is entered into the memory 52 (FIG. 2) at the location of the CPU-based supervisory system 20 (FIG. 1) for each officer and agency that is enrolled.

Still continuing with the enrollment process (block 70 of FIG. 3), once the agencies and officers are properly enrolled, those being supervised by the system are enrolled by the officers of the agency. If those being supervised by the system are parolees or probationers, such may be referred to herein as "offenders". However, it is to be emphasized that the present invention has much wider applicability than just supervising offenders. Any group of persons or individuals requiring supervision, such as students, elderly people living alone, handicapped persons, persons needing specific health care, etc., may benefit from the PSS described herein. Thus, those being supervised will typically be referred to herein as "enrollees", and those doing the supervision are referred to as "officers".

The officers provide enrollment data or information for each enrollee that is to be enrolled in the system. Such enrollment data may be transferred to the memory 52 of the CPU-based host supervisory system 20 using any suitable means, e.g., downloading through a modem connection from a remote site. The enrollment data includes: (1) the enrollee name; (2) the enrollee's assigned telephone number, including area code; (a) a personal identification number (PIN); (4) a password; (5) the officer's name; (6) the officer's PIN; (7) the agency code; (8) the call-in schedule; and (9) an authorized DNIS code (issued by the telephone company so as to tie a particular fee to a specific 900 number). The enrollment data may further include an indication as to the language spoken and understood by the enrollee. If the enrollee is an offender, then additional enrollment data may include: (10) the offender's case number; (11) the judge; (12) the first call-in date; (13) the last call-in date; and (14) a grace period (days allowed without calling in on schedule before a missed call report will be issued to the assigned officer). The critical information needed by the enrollee is the 900 number that is to be called, the schedule when calls are to be made (e.g., once a month), the enrollee's PIN and assigned password, and an identification of the telephone number of the telephone line from which the enrollee is to make his or her calls when reporting to the system. Much of this information can be placed on a convenient wallet-sized card that the enrollee can keep with him or her, or in another known location. It is assumed, of course, that the enrollee will also be informed (and consent to, either by agreement or court order) of the supervision fee that will be charged each time a call is made to the system in accordance with the assigned schedule.

Still referring to FIG. 3, once all the enrollment data has been entered into the memory of the host CPU, the personnel supervisory system (PSS) operates by waiting for the enrollee to telephone ("call in") to the host CPU in accordance with the assigned schedule (block 72). At the scheduled time to call, a given enrollee calls the PSS through the appropriate 900 number (block 74). The PSS connects with each call received (block 76) and determines, before going off-hook (i.e., before formally answering the call) if the incoming call is a valid call (block 78). The manner in which this determination is made is described below in FIG. 5. If the incoming call is not a valid call, then the host CPU momentarily goes "off-hook" (answers the call) and a message is generated by the speech generation module 56 (FIG. 2) that informs the caller why the call is not valid (block 80). Then the call is ended (block 82) before the expiration of the preamble time period, thereby preventing a toll fee from being charged (block 84) to the caller. The system then waits for the next call to come in (block 72).

If the call is a valid call (as determined at block 78), then the system goes off-hook and remains off-hook sufficiently long for the preamble time period to expire, thereby causing the assigned toll-fee to be automatically charged to the calling party (block 86). As soon as the system goes off-hook, which could be before the expiration of the preamble time period, the host CPU (using the speech generation module) may request that further identification be provided by way of the enrollee's PIN and/or password. For some types of enrollees, i.e., those who might try to enlist the aid of a friend to call-in for them, the system may further identify the caller using voice prints of the enrollee that have been stored during the enrollment process. Typically, when voice identification is used, the enrollee records a series of phonetic utterances, e.g., a group of words, during enrollment. During verification, the caller is asked to repeat a randomly selected group of such utterances or words. If the voice print of the caller's words substantially matches that of the recorded words, then the identity of the caller is verified. Other types of identification may also be used, in addition to, or in lieu of, the PIN, password or voice print identification techniques described above, such as electronic fingerprints, video images, encoded cards (which may be affixed to the individual, e.g., in a bracelet), or the like.

Once a valid PIN/password combination has been received, and any other verification tests have been successfully passed, the PSS asks the enrollee to state his or her name. Any response to a request to state a name is recorded and such recording is made available to the assigned officer upon request. The PSS also prompts the enrollee for new status information (block 88). Advantageously, such prompts are made by way of a series of questions that can be answered with a YES or a NO. The caller replies to the questions by using a combination of simple YES/NO touchtone keypad entries (e.g., press 1 for YES, and 2 for NO) and/or spoken information. For each question to which the caller replies that indicates no status change (i.e., no new information to report), the system advances to the next question (blocks 90, 96). For each question to which the caller replies that indicates a status change (i.e., there is new information to report), the caller provides such new information (block 92), and such new information is recorded (block 94).

An example of types of questions that may be used by the PSS to prompt a caller who is an "offender" is as follows:

1. Has you home address changed since you last checked in?
2. Have you changed jobs since you last checked in?
3. Have you had any police contacts or been rearrested since you last checked in?
4. Are you following the specific special conditions of your supervision?
5. Have you missed your last payment on your court-ordered financial obligations, including your supervision fee?

As evident from the above exemplary questions, a negative (NO) response to each question, except question 4, causes the system to advance to the next question. Question 4 requires an affirmative (YES) response in order to advance to question 5.

Should a caller, for example, answer YES in reply to question 1, the system would respond with "After the beep, please clearly state your new home address including city, state and zip code." A beep would then be heard, and the caller would state his new address as requested. Such information is then recorded for later transcription by agency personnel.

As an additional feature, the PSS system may be configured to offer callers a prescribed amount of time, e.g., four seconds, to reply to a specific query for numeric input (but not a spoken response to a question requiring an explanation) before being told to "Please enter your response more quickly". Callers are told to enter a response more quickly two or three times during a single question. If the response does not come within the prescribed time period, e.g., four seconds of the second instruction to speed the process, the call is automatically disconnected and an appropriate report may be logged and delivered to the assigned officer. Repeated slow responses may be an indication, for example, that the enrollee is suffering from a debilitating medical condition, or is under the influence of alcohol or drugs.

Figure 4:
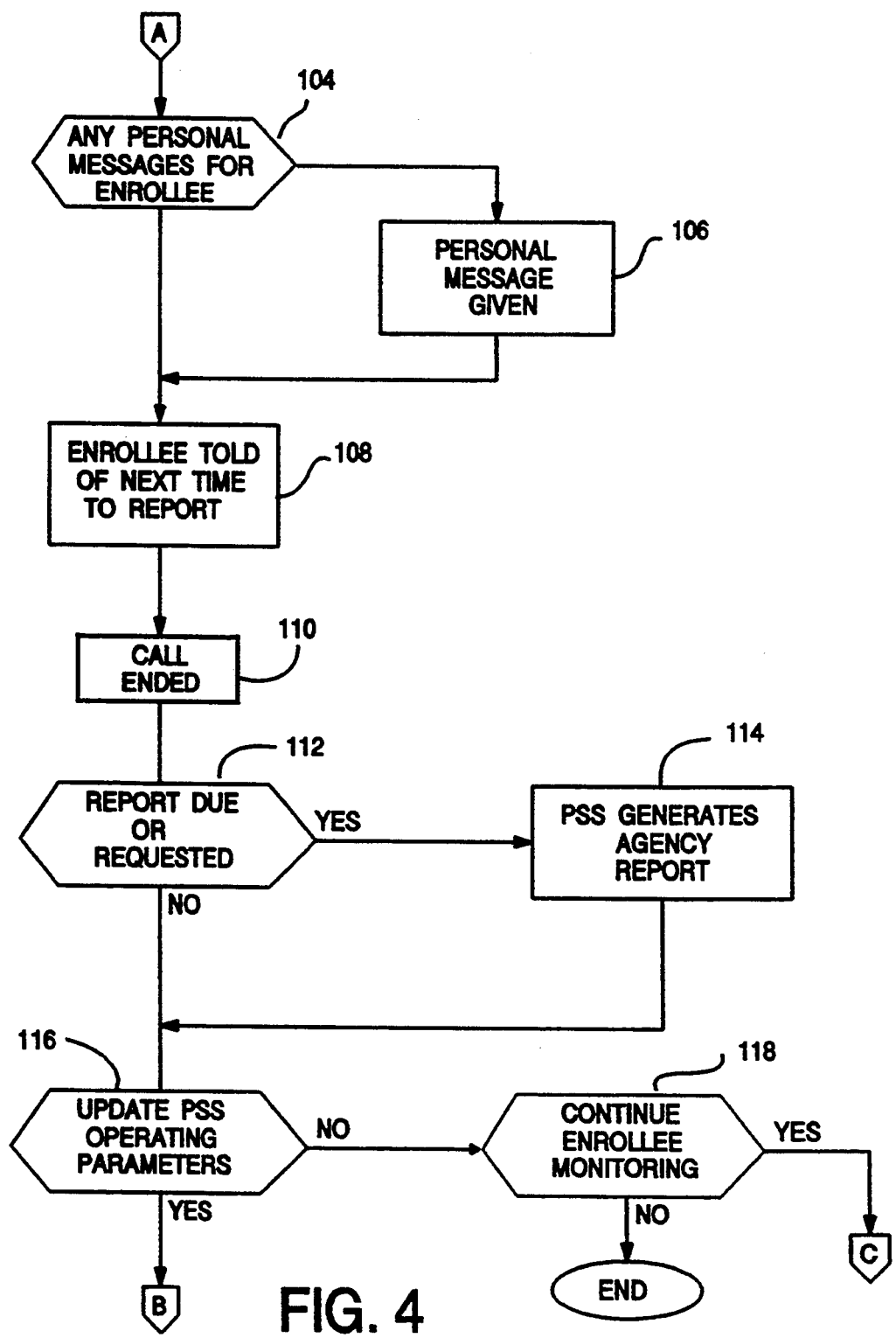
FIG. 4 is a continuation of the flow chart of FIG. 3.

Turning next to FIG. 4, which is a continuation of FIG. 3, the PSS allows officers to leave a personal, recorded voice message for any specific enrollee assigned to such officer. The PSS determines whether there are any such personal messages for the particular caller who is calling (block 104). Such personal messages may be used, e.g., by an officer to remind an offender of an upcoming court date, a meeting with the officer, to announce and schedule upcoming drug tests, or the like. If a personal message has been prepared for the enrollee, such message is played back for the caller (block 106). The PSS then reminds the caller of the next scheduled call-in date (block 108). Such reminder may take the form, for example, of: "Your next scheduled call-in will be on (MONTH), (DATE). Please make a note of it." The call is then terminated (block 110). Typically, the PSS will state "Good-by" immediately prior to ending the call. When a call is completed and terminates in this manner, the PSS logs the call as "complete" call. Should a call be received that is billable (a call that lasts longer than the preamble time period) but which is terminated before the call is complete, e.g., because the caller responded too slowly, then such call is logged as a "billed and incomplete" call.

As stated above, the prescribed toll fee is automatically charged to any incoming call that lasts longer than the preamble time period. For 900 telephone service offered through American Telephone and Telegraph (AT&T), the preamble time period is 18 seconds. Thus, the caller is charged the toll amount for any call which lasts longer than 18 seconds. A typical valid call, wherein the caller responds to the questions that are asked, will usually take around two (2) minutes or more.

The PSS advantageously logs each call received, both complete and incomplete calls, as well as valid and invalid calls. Further, any new information provided during the call is stored for a prescribed time period, e.g., six years, or until suitably transcribed and archived. The information contained in such logs may be appropriately compiled and included in reports that are used by the agency to keep track of the enrollees, and to monitor the performance of the PSS. For example, periodic reports may be issued that statistically identify how many incoming calls are invalid because there is no match in the data base, or how many incoming calls are invalid because the caller has already called in during the reporting period. Other reports may identify incomplete calls, or other information associated with the received calls, or associated with a particular enrollee or group of enrollees. Each officer, for example, may request, or periodically receive, a report that identifies those enrollees who failed to report on schedule, those who did report on schedule, and those who have indicated a change in status. For those who have indicated a change in status, the officer can listen to the new status information stated by the enrollee, and respond accordingly. A normal response to updated status information would be to transcribe the information so that it can be entered into the memory of the host CPU. The officer may also want to personally contact the enrollee to verify some aspect of the updated status information. In this manner, prescribed reports, such as compliance and non-compliance reports, or other needed reports, may be automatically generated by the PSS at prescribed intervals or upon request (blocks 112, 114 of FIG. 4). Further, the PSS operating parameters may be updated (block 116) with any new information, as required.

Figure 5:
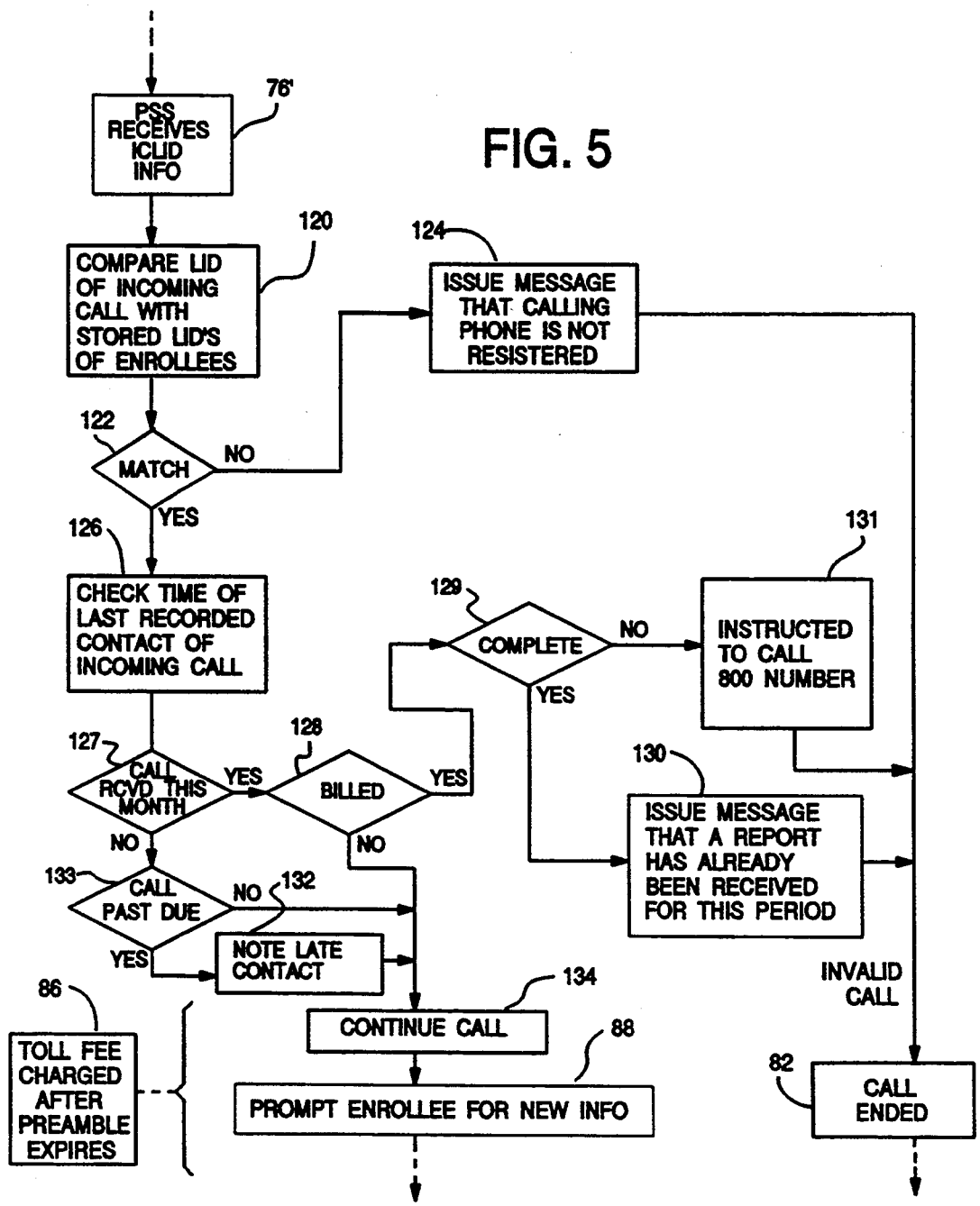
FIG. 5 is a more detailed flow chart illustrating how the supervision system of FIGS. 3 and 4 responds to an incoming telephone call.

Turning next to FIG. 5, a more detailed flow chart is presented of the manner in which the PSS determines in an incoming call is a valid or an invalid call. Such determination is shown in FIG. 3 as a single step (block 78). However, in practice, such determination is made by performing a sequence of steps. Once the PSS connects with the first incoming ring, and assuming that "Caller ID" technology is being used, it receives the incoming call line identification (ICLID) information that is provided after the first ring (block 76'), as explained previously. Such ICLID identifies the telephone number of the incoming call. The line ID (LID) of the incoming call is then compared with the telephone numbers of the valid enrollees that are stored in the enrollee database in the memory of the host CPU (block 120). If there is no match, i.e., in the LID of the incoming call is not found in the enrollee data base, then a message is issued to the caller that states that the calling phone is not registered (block 124) and the call is ended (block 82). The message issued by the PSS may state, for example, "Your calling telephone is not registered to (Name of Agency). Please contact your supervising officer if you have been instructed to call this telephone number." Advantageously, the message is given and the call is ended before the expiration of the preamble time period, e.g., the message is delivered in less than 18 seconds, so no toll fee is charged to the caller.

If there is a match between the ICLID and the telephone numbers of the enrollees as stored in the host CPU memory (as determined at block 122), then the PSS checks to determine the last recorded contact of an incoming call from the identified telephone number (block 126). If the present call is early, i.e., if there has been a prior call received from the identified telephone within the reporting period, (block 127) and if the prior call was a completed call (block 128), then another message is issued that a report has already been received from this telephone number during the reporting period (block 130). As a result, the call is considered to be an invalid call, i.e., a redundant or "dummy call". Thus, the call is ended (block 82) before the expiration of the preamble time period, and the caller is not charged the toll fee. The message issued by the PSS may state, for example, assuming that the enrollee is required to call in once a month, "A report has been received this month from this telephone. Please call again next month."

In the event that an incoming call has already been received (block 127) and such call was billed (block 128), but was not complete (block 129), then that is an indication that a mistake or other problem occurred during the prior call. In such instance, a message is generated advising the caller to call a specific 800 number (toll free) (block 131). The call is then ended (block 82) before the timing out of the preamble time period, thereby preventing the caller from being charged the toll fee for the second call. The caller can then call the 800 number (which is only authorized for use by the CPU in specific situations, i.e., when a mistake has been made) in order to correct the mistake or complete the information not provided during the incomplete call. As needed, the caller may also make contact with an operator via an 800 helpline. While the initial, incomplete call results in billing of the 900 service fee, the second call via the 800 (toll free) will not cost the caller anything. Thus, the toll fee is charged to the enrollee Just once for the reporting period.

In the event that an incoming call is from a valid telephone number but is late (blocks 127, 133), then such fact may be noted (block 132) and the call is allowed to continue (block 134), meaning that the caller is prompted for his or her name and any new information (block 88). The lateness of the call may then be included in the report issued to the agency, so that it can respond accordingly, e.g., by leaving a message for the enrollee to call the officer and explain why the call was late.

In the event that the incoming call is from a valid telephone number and is received in accordance with the prescribed call-in schedule (block 127), then the incoming call continues (block 134) and the enrollee is prompted for his or her name and any new information (block 88) as described above in FIG. 3.

Regardless of whether the incoming call is past due or not, as the call continues, and the enrollee is prompted for the requested information, the preamble time period eventually expires, and the toll fee is automatically charged to the enrollee (block 86). That is, when using the 900 toll fee service, the prescribed fee is assessed by AT&T when the call duration exceeds 18 seconds. The charge then appears on the monthly telephone bill issued by the local telephone service, and the enrollee pays the fee as part of the normal telephone bill. Should the enrollee terminate a call before the PSS states "Good-by", the toll fee will be assessed, even though the data collected during the call may not be transcribed and reported. Thus, it is in the best interest of the enrollee to not prematurely terminate an incoming call.

At the end of the month, the telephone company, or other agency that collects the fees for the telephone bills, prepares a remittance report and sends a check to the monitoring agency, or other service company responsible for collecting the supervision fees. The service company that performs the monitoring may also prepare specific reports for each agency, detailing a list of all callers that completed a call to the host CPU during the reporting period, a list of all calls and charges disputed and refunded by the appropriate agencies and/or telephone companies during the reporting period, and an accounting of the total charges received by the service company, less any charges refunded due to disputes.

As mentioned above, the host CPU-based supervisory system 22 (FIGS. 1 and 2) may actually include a network of CPU's linked together via a suitable local area network (LAN), such as is commercially available from numerous LAN companies, e.g., Novell. By way of example, such LAN may include a central file server that functions as the main information gathering point of the system and, as such, is configured to run continuously. The server may run, e.g., under Novell's System Fault Tolerant II (SFT) version of Netware 386 on an NCR Model 925 CPU. The NCR 925 is an Intel 386-based computer configured with 8 megabytes of main memory and 1.2 gigabytes of hard disk storage (mirrored and duplexed). The SFT software, which is known and described in the literature, provides for data duplication of all information stored on the hard disks.

Coupled to the server are one or more call processing stations (CPS). The CPS's are the workhorses of the personnel supervisory system. Each is equipped with commercially available voice processing cards, available, e.g., from Dialogic as model D41B and VR10, and each is controlled with appropriate software that carries out the in-coming call operation detailed in FIGS. 3–5. Each CPS is capable of processing calls from touchtone and rotary telephones, with all responses being stored on the central file of the server. The CPS's may be realized using an NCR 386sx computer configured to handle 4 or 8 simultaneous calls.

Also coupled to the server is an administrative station. The administrative station acts as the central point of operation for the PSS. It is from the administrative station that the system activity may be monitored, agency reports are processed and data entry and transcription efforts are performed. The administrative station also may double as the modem communications point for agencies that make use of electronic data transfer capabilities. That is, a given officer may collect enrollment data at a field location, and then transfer the enrollment data to the PSS by modem through the administrative station.

Additionally coupled to the server may be a transcription computer. Such transcription computer controls and manages all enrollee or officer recorded responses that are played back for transcription. The transcription computer is thus essentially a digital version of a dictating device, providing play, cue forward, cue back, pause, cue-to-start, and other commonly used controls used during the transcription process.

Advantageously, all of the hardware components needed in such a CPU supervisory system are readily available from numerous commercial sources at a modest cost; and are easy to install and maintain.

As described above, it is thus seen that the invention provides a supervisory system and method that allows a probation officer, or other supervisory personnel, to effectively handle and supervise a large caseload using a system that is relatively inexpensive to acquire and easy to install, operate and maintain.

It is also seen that the invention provides such a supervisory system that automatically charges a prescribed fee for the supervisory services provided by the system.

Moreover, it is seen that the invention provides a fee-based supervisory system wherein supervisory personnel are free to spend their time in supervising those enrolled in the system, and do not have to spend any time in collecting supervision fees.

It is further seen that such supervisory system, while having wide applicability to many situations, is especially well suited to the corrections industry, allowing probation officers and corrections professionals to monitor a large caseload of probationers and/or parolees, while at the same time automatically charging an appropriate fee to the probationers and/or parolees who are thus monitored, being capable of regularly or on command generating reports showing the status and compliance with mandated reporting schedules of all or selected enrollees.

While the invention herein disclosed has been described by means of specific embodiments and applications thereof, numerous modifications and variations could be made thereto by those skilled in the art without departing from the scope of the invention set forth in the claims.

What is claimed is:

1. An adaptable personnel supervisory system (PSS) comprising:

a fee-based communication network that automatically charges a toll fee to a user thereof once telecommunicative contact has been established through the fee-based communication network with a host unit for a specified preamble time period;

a central processing unit (CPU) coupled to said fee-based communication network;

a memory coupled to said CPU having enrollment data stored therein that identifies enrollees who are under an obligation to contact said PSS in accordance with a prescribed contact schedule; and control means for controlling the operation of said CPU to provide a specified supervisory function, said control means including:

answering means for automatically answering an incoming call over said fee-based telephone network, call verification means for verifying before the expiration of said preamble time period whether the incoming call is a valid call, and if not for terminating the incoming call before the toll fee is charged, a valid call comprising an incoming call from one of said enrollees in accordance with the prescribed contact schedule, whereby the toll fee is not charged unless the incoming call is valid, prompting means responsive to said verifying means for prompting a given enrollee who has made a valid call to said PSS to provide selected information, recording means for recording any selected information provided by the given enrollee in response to the prompting means, and report means for selectively generating host reports that selectively identify which enrollees have not made contact with the host unit, which enrollees have made contact with the host unit, and the selected information provided by the enrollees who have made contact with the host unit;

whereby each enrollee is automatically charged the toll fee whenever he or she contacts the PSS by means of a valid call placed through said fee-based communication network in compliance with said prescribed contact schedule.

2. The adaptable PSS as set forth in claim 1 wherein said verifying means includes source identification means for determining the location from which the incoming call originates, and comparison means for comparing such location with a list of valid locations stored within the memory of said CPU, the incoming call being designated as a valid call by said verifying means only when the location of the incoming call matches one of the valid locations stored within the memory of the CPU.

3. The adaptable PSS as set forth in claim 2 wherein said communication network includes a public telephone network, and further wherein the memory of said CPU has a list of valid telephone numbers belonging to enrollees of said PSS stored therein; and wherein said source identification means comprises means for identifying the telephone number of the incoming call, and said comparison means includes means for comparing the telephone number of the incoming call with said list of valid telephone numbers stored in the memory of said CPU, the incoming call being designated as a valid call by said verifying means only when the telephone number of the incoming call matches one of the valid telephone numbers stored within the memory of the CPU.

4. The adaptable PSS as set forth in claim 3 wherein said verification means further includes means for determining if a given incoming call is from a telephone number from which a valid call has already been received by the PSS during a current contact period of the prescribed contact schedule, and for classifying the given incoming call as an invalid call if a valid call has already been received from the telephone number of the incoming call during the current contact period in accordance with the prescribed contact schedule, whereby the enrollee is limited to making one valid call to the PSS during each contact period of the prescribed contact schedule, and further whereby the toll fee may only be charged once during each contact period of the prescribed contact schedule.

5. The adaptable PSS as set forth in claim 4 wherein said verification means further includes means for issuing a prescribed message in the event that the incoming call is not a valid call, said prescribed message informing a caller why the incoming call is not considered to be a valid call.

6. The adaptable PSS as set forth in claim 4 wherein said prompting means includes means for issuing a series of questions to said enrollee that can be answered with a YES or a NO answer, and wherein said recording means includes means for storing the YES or NO answers given by a particular enrollee.

7. The adaptable PSS as set forth in claim 6 wherein said means for recording further includes means for allowing the enrollee to provide additional information to supplement a prescribed one of the YES or NO answers.

8. The adaptable PSS as set forth in claim 4 wherein said memory further has officer data stored therein that identifies at least one supervisory officer responsible for supervising a group of said enrollees, and further wherein said report means includes means for selectively issuing reports to said at least one supervisory officer that selectively identifies: which of the enrollees in said group of enrollees have not made contact with the host unit in accordance with the prescribed contact schedule, which enrollees in said group have made contact with the host unit in accordance with the prescribed contact schedule, and the selected information provided by the enrollees in the group who have made contact with the host unit.

9. The adaptable PSS as set forth in claim 8 wherein said PSS further includes means for said at least one supervisory officer to store a personal message in said PSS, and wherein said prompting means includes means for providing said personal message to a specified enrollee in said group of enrollees at the time the specified enrollee establishes a valid call with the PSS in accordance with the prescribed contact schedule.

10. An adaptable personnel monitoring and identification system for monitoring the status of a group of enrollees, each enrollee in said group of enrollees being obligated to regularly report his or her status, said system comprising:

a telephone network, said telephone network including means for providing individual calling line identification (ICLID) information on all telephone calls;

a central processing unit (CPU) coupled to said telephone network, said CPU having a memory wherein status information relating to each enrollee in said group of enrollees is stored, said status information including at least the enrollee's name and address;

means for a given enrollee to establish telecommunicative contact with said CPU from a telephone coupled to said telephone network;

said CPU having an administrative case load management control program stored therein that controls said CPU for the purpose of automatically verifying the status of the given enrollee of said group of enrollees once contact with said CPU has been established through said telephone network, and a speech generation module for prompting the given enrollee with specific instructions;

said administrative case load management control program including means for automatically: (1) verifying the identity of said given enrollee once telecommunicative contact is established with said CPU, (2) verifying that the given enrollee has contacted the CPU within an obligated contact time period, and (3) verifying whether there has been a change in the status of the given enrollee since the status information was last stored in the CPU memory.

11. The adaptable personnel monitoring and identification system as set forth in claim 10 wherein said administrative case load management program controls said CPU to instruct the given enrollee in telecommunicative contact with said CPU to uniquely identify himself or herself, and to allow such enrollee to update his or her status if there has been a change in his or her status since last contacting said system.

12. The adaptable personnel monitoring and identification system as set forth in claim 11 wherein said administrative case load management program includes means for uniquely identifying said given enrollee based on an assigned personal identification number.

13. The adaptable personnel monitoring and identification system as set forth in claim 11 wherein said administrative case load management program includes means for uniquely identifying said given enrollee based on his or her voice.

14. The adaptable personnel monitoring and identification system as set forth in claim 11 wherein said administrative case load management program includes means for identifying a location at which the given enrollee is located at the time when said telecommunicative contact is established.

15. The adaptable personnel monitoring and identification system as set forth in claim 14 wherein said administrative case load management program further includes means for verifying whether said location at which said given enrollee is at when in telecommunicative contact with said system is an assigned location.

16. The adaptable personnel monitoring and identification system as set forth in claim 15 further including means for automatically charging the given enrollee a prescribed fee once the location of the given enrollee at the time of the telecommunicative contact has been verified as an assigned location.

17. The adaptable personnel monitoring and identification system as set forth in claim 16 wherein said prescribed fee is charged only after said administrative case load management program has verified that the given enrollee has contacted the CPU within the obligated contact time period.

18. An adaptable personnel monitoring and identification system for monitoring a population of individuals comprising:
  means for establishing telecommunicative contact between a given individual of said population of individuals, under obligation to make regular status reports, and a central processing unit (CPU), said CPU having status information stored therein for each individual of said population of individuals being monitored;
  an administrative case load management program stored in said CPU, said administrative case load management program including: (1) means for verifying the identity of said given individual once telecommunicative contact is established with said CPU, and (2) means for automatically requesting from the given individual whether the status information stored in said CPU for said given individual has changed since said given individual last contacted said CPU; and
  means for automatically charging said given individual with a prescribed fee once the identify of the given individual has been verified.

19. The personnel monitoring and identification system as set forth in claim 18 wherein said administrative case load management program further includes means for allowing said given individual to change the status information stored in said CPU in the event such status information has changed.

20. The personnel monitoring and identification system as set forth in claim 19 wherein said verifying means of said administrative case load management program includes means for verifying that a personal identification number (PIN) provided by said given individual, once telecommunicative contact has been established, is a valid PIN.

21. The personnel monitoring and identification system as set forth in claim 19 wherein said verifying means of said administrative case load management program includes means for verifying that a voice response provided by said given individual once telecommunicative contact has been established is a voice response unique to said given individual.

22. The personnel monitoring and identification system as set forth in claim 19 wherein said verifying means of said administrative case load management program includes means for verifying that said given individual is at a prescribed geographic location when said telecommunicative contact is established.

23. A method of automatically charging a fee to an enrollee of a supervisory system whenever said enrollee makes telephone contact with a host CPU of said supervisory system pursuant to a prescribed telephone contact schedule, said method comprising the steps of:
  (a) assigning a specific fee-based telephone number to said host CPU, said fee-based telephone number being controlled through a telephone network to automatically charge a prescribed fee to a caller who calls the specific fee-based telephone number and remains in contact with the host CPU via said specific fee-based telephone number for more than a prescribed preamble time period;
  (b) storing enrollment data in a memory of said host CPU that identifies each enrollee and his or her telephone number from which the specific fee-based telephone number is to be called;
  (c) monitoring the incoming calls received at said host CPU through said specific fee-based telephone number during said preamble time period to determine if said incoming calls have originated from an enrollee's telephone number stored in the memory of the host CPU;
  (d) automatically disconnecting, prior to the timing out of said preamble time period, any incoming call received through said specific fee-based telephone number that did not originate from one of the enrollee's telephone numbers stored in the memory of the host CPU as determined in step (c), whereby said prescribed fee is not charged to an incoming call from any number other than one of said enrollee's telephone numbers;
  (e) generating a speech message at said host CPU in response to any incoming call received through said specific fee-based telephone number that did originate from one of the enrollee's telephone numbers stored in the memory of the host CPU as determined in step (c), said speech message instructing said given enrollee how to inform the host CPU of his or her current status, including whether such status has changed since the given enrollee last contacted the host CPU, said speech message and any corresponding response from the given enrollee lasting longer than said preamble time period, whereby said prescribed fee is charged to an enrollee who places an incoming call to said host CPU through said specific fee-based telephone number.

24. The method as set forth in claim 23 wherein said method further includes:
  (f) recording within the memory of said CPU a record of those enrollees who have contacted the host CPU by telephone in accordance with the prescribed telephone contact schedule;

(g) updating the enrollment data within the memory of said CPU with any new status information provided in response to the speech message generated in step (e);

(h) comparing the record made in step (f) with the enrollment data stored in the memory of the host CPU for the purpose of determining which of the enrollees has not made telephone contact with the host CPU in accordance with the telephone contact schedule; and (i) regularly generating a report that selectively identifies which enrollees have not made contact with the host CPU, which enrollees have made contact with the host CPU, and the status of any enrollee.

25. The method as set forth in claim 24 wherein said prescribed telephone contact schedule requires each enrollee to make telephone contact with said host CPU once and only once during a prescribed contact period, and wherein step (d) further includes automatically disconnecting, prior to the timing out of the preamble time period, any incoming call received through said specific fee-based telephone number that originated from an enrollee's telephone number from which a telephone contact has already been made, as determined by the record made in step (f), during the present prescribed contact period, whereby said prescribed fee is not charged to more than one incoming call from a specific enrollee's telephone number during a given prescribed contact period.

26. The method as set forth in claim 25 further including generating an appropriate speech message prior to the disconnecting of an incoming call in step (d) that informs the enrollee why the incoming call is being disconnected.

27. The method as set forth in claim 25 further including verifying that the caller who contacts the host CPU using said specific fee-based telephone number from a given enrollee's telephone number is an individual enrolled in said supervisory system.

28. The method as set forth in claim 27 wherein said step of verifying includes said caller entering a personal identification number (PIN) into said host CPU during said telephone contact, and comparing said entered PIN with an assigned PIN for the given enrollee's telephone number included in said enrollment data.

29. The method as set forth in claim 27 wherein said step of verifying includes comparing a voice print of said caller to a previously stored voice print obtained from the enrollee assigned to the telephone number from which the telephone contact originates.

30. The method as set forth in claim 25 wherein the speech message generated in step (e) includes a series of questions that may be answered with a YES or NO answer relative to the status of the enrollee.

31. The method as set forth in claim 30 wherein the enrollee answers the series of questions generated in step (e) by activating an appropriate key or number of a telephone used by the enrollee to establish said telephone contact, with a first specific key or number representing a YES answer, and a second specific key or number representing a NO answer, said telephone generating respective electrical YES and NO signals that are received and stored in said host CPU.

32. The method as set forth in claim 25 further including generating a personal speech message for a specific enrollee during the time that said specific enrollee has made telephone contact with said host CPU in accordance with the prescribed telephone contact schedule.

33. The method as set forth in claim 32 wherein said personal speech message includes a reminder that informs the enrollee when he or she is next scheduled to contact the host CPU.

* * * * *